(12) United States Patent
Bombardelli et al.

(10) Patent No.: US 8,940,338 B2
(45) Date of Patent: Jan. 27, 2015

(54) FORMULATIONS FOR THE TREATMENT OF MUCOSITIS INDUCED BY ANTITUMOR OR IMMUNOSUPPRESSIVE THERAPY

(75) Inventors: Ezio Bombardelli, Groppello Cairoli (IT); Gabriele Fontana, Milan (IT)

(73) Assignee: Indena S.p.A., Milan (IT)

( * ) Notice: Subject to any disclaimer, the term of this patent is extended or adjusted under 35 U.S.C. 154(b) by 695 days.

(21) Appl. No.: 12/812,065

(22) PCT Filed: Jan. 8, 2009

(86) PCT No.: PCT/EP2009/000050
§ 371 (c)(1),
(2), (4) Date: Aug. 3, 2010

(87) PCT Pub. No.: WO2009/087091
PCT Pub. Date: Jul. 16, 2009

(65) Prior Publication Data
US 2010/0284945 A1      Nov. 11, 2010

(30) Foreign Application Priority Data

Jan. 11, 2008  (IT) ............... MI2008A0038

(51) Int. Cl.
| A61K 31/4355 | (2006.01) |
| A61K 9/68 | (2006.01) |
| C07D 491/22 | (2006.01) |
| A61P 1/04 | (2006.01) |
| A61P 29/00 | (2006.01) |
| A61P 15/02 | (2006.01) |
| B60S 3/06 | (2006.01) |

(52) U.S. Cl.
CPC ....................................... B60S 3/063 (2013.01)
USPC ............. 424/573; 424/48; 514/279; 514/280; 546/41; 546/48

(58) Field of Classification Search
CPC ......................................................... A61K 8/02
USPC ........................................................... 424/49
See application file for complete search history.

(56) References Cited

FOREIGN PATENT DOCUMENTS

| EP | 0 565 495 | | 10/1992 |
| JP | 2000109428 A | * | 4/2000 |
| WO | 2006/063716 | | 6/2006 |
| WO | WO 2006063716 A1 | * | 6/2006 |
| WO | 2007/047003 | | 4/2007 |
| WO | 2008/012666 | | 1/2008 |
| WO | 2009/103476 | | 8/2009 |

OTHER PUBLICATIONS

Lenfeld, J. et al. "Anti-Inflammatory activity of Quaternary Benzophenanthridine Alkaloids from Chelidonium-Majus" Planta Medica, vol. 43, No. 2, 1981, pp. 161-165.
Lalone, C. et al. "Echinacea species and alkamides inhibit prostaglandin E-2 production in RAW264.7 mouse macrophage cell" Journal of Agriculture and Food Chemistry, vol. 55, No. 18, Sep. 5, 2007, pp. 7314-7322.
Karp, J. et al. "Sanguinarine activates polycyclic aromatic hydrocarbon associated metabolic pathways in human oral keratinocytes and tissues" Toxicology Letters, vol. 158, No. 1, Jul. 28, 2005, pp. 50-60.

* cited by examiner

*Primary Examiner* — Walter Webb
(74) *Attorney, Agent, or Firm* — Silvia Salvadori, P.C.

(57) ABSTRACT

Formulations containing sanguinarine or chelerythrine or the salts thereof or extracts containing them in admixture with suitable carriers and/or excipients for the treatment and/or prevention of mucositis.

11 Claims, No Drawings

FORMULATIONS FOR THE TREATMENT OF MUCOSITIS INDUCED BY ANTITUMOR OR IMMUNOSUPPRESSIVE THERAPY

This application is a U.S. national stage of PCT/EP2009/000050 filed on Jan. 8, 2009 which claims priority to and the benefit of Italian Application No. MI2008A38 filed on Jan. 11, 2008, the contents of which are incorporated herein by reference.

The present invention relates to pharmaceutical formulations useful in the treatment of mucositis induced in humans by chemotherapy, radiotherapy and treatment with systemic immuno-suppressors.

The formulations of the invention contain free or salified benzophenanthridine alkaloids and suitable carriers, depending on the various parts of the patient body to treat. Said alkaloids have strong antimicrobial, antifungal, anti-inflammatory, analgesic, immunostimulating, antiangiogenetic and an antiproliferative action selective for cancer cells and are capable of reducing or preventing mucositis.

The invention further relates to the salts of said alkaloids with luteic acid.

TECHNOLOGICAL BACKGROUND

Severe forms of painful mucositis often occur both in oncology and organ or bone marrow transplantation with concomitant immunosuppressive therapy. They can only be counteracted by systemic analgesics, in particular opioids, combined with heavy support therapies. In many cases, onset of severe mucositis is the cause of suspension of chemotherapeutic treatments, thus allowing the tumor to continue its growth.

Radical treatments can induce side effects mainly affecting the gastrointestinal tract, particularly the mouth, esophagus, stomach, intestine and in some cases even the genito-urinary tract.

Medicaments which most frequently induce mucositis are anthracyclines, fluorouracil and analogues; and others, such as taxol, actynomicin, mithramycin, etoposide, topotecan, amsacrine, methotrexate, hydroxyurea, alone or in combination with other chemotherapeutics such as platinum complexes commonly used in cancer therapy. The combination of chemo- and radio-therapy in some districts, such as in head and neck therapy, causes mucositis in 95% of treated patients.

Conventional treatments for mucositis involve the administration of non-gastrolesive anti-inflammatory agents, analgesics, antimicrobials, antifungals, H2 antagonists and protective gels which help to maintain the affected area hydrated. Local pain is a side-effect which restricts the rational administration of the other drugs. The patient under such conditions experiences difficulty to eat, which leads to weight loss, dehydration and severe health impairment.

DISCLOSURE OF THE INVENTION

It has now surprisingly been found that the benzophenanthridine alkaloids sanguinarine and chelerythrine are advantageously effective in reducing and/or preventing the onset of mucositis induced by oncological or immunosuppressive treatment.

Therefore the invention provides formulations containing sanguinarine or chelerythrine or salts thereof or extracts containing them, in admixture with suitable carriers and/or excipients, for the treatment and/or the prevention of mucositis.

Sanguinarine or chelerythrine can be present in a substantially pure form or in the form of extracts of *Sanguinaria canadensis, Macleaya cordata* or *Macleaya macrocarpa*.

The invention further relates to the use of sanguinarine or chelerythrine or salts thereof or extracts containing them for the preparation of medicaments for the treatment and/or prevention of mucositis.

Furthermore it has been found, and this is a further object of the invention, that the salts of these alkaloids with luteic acid are particularly effective for the purposes of the present invention.

The salts of the invention are prepared by reaction of the alkaloids sulfates or chlorides with luteic acid sodium or potassium salt and subsequent crystallization.

Said salts, particularly the sanguinarine salt, exert antiphlogistic, analgesic, antiangiogenetic, antimicrobial, antifungal, cicatrising and antiproliferative action on both sensitive and resistant cells.

Luteic acid gives the alkaloid different bioavailability and increased antiviral activity, particularly against Citomegalovirus, Papillomavirus, Rhinovirus, Adenorinovirus, Herpes zoster and Herpes simplex; furthermore, luteic acid reduces bacterial and fungal adhesion to cells, thereby enhancing the antimicrobial and antifungal effect of the alkaloids.

This aspect is particularly advantageous in that mucositis is often associated with bacterial and/or fungal infections.

The formulations of the invention can further contain isobutylamides extracted from *Echinacea angustifolia* or synthesized from polyunsaturated acids, which have agonistic action on CB1 and CB2 cannabinoid receptors. Both natural and synthetic isobutylamides, when administered concomitantly with the radio-chemotherapeutic treatment, reduce the appearance of nausea and vomit which affect almost all of the treated patients, and this is a further particularly advantageous aspect of the invention.

The active principles contained in the formulations of the invention show negligible absorption through the oral route and can therefore be administered prophylactically, before the administration of the chemotherapeutic, or between chemotherapy cycles.

The compositions of the invention are able to reduce peripheral oncological pain already within 20 minutes; to prevent the formation of purulent plaques infected by saprophytes in the oral cavity, avoiding the use of antibiotics while reducing the progress of the infection; to reduce the severity of the fungal infections and to contribute to restoration of mucus barriers.

The pharmaceutical compositions can be in the form of tablets, capsules or chewable tablets, chewing gums, creams, ointments, foams, vaginal suppositories.

Tablets with slow dissolution in the oral cavity or chewable gums can be suited when the slow release of the active principles is desired.

According a preferred aspect, the formulations of the invention will further contain essential oils to increase the patient compliance in terms of freshness of the oral cavity.

The effective dosages of sanguinarine and chelerythrine in the compositions of the invention can range from 1 to 20 mg, either in the free or salified form; the same alkaloids and the salts thereof can be solubilised in slow release gels consisting of proteoglycans or substituted celluloses. The alkaloids can be incorporated in patches to be applied to the palate for the treatment of subjects with experience difficulty in using conventional formulations.

Suitable formulations for the treatment of mucositis of the digestive tract comprise tablets, capsules or dispersible granulates which promote adhesion to the gastro-intestinal walls. For the treatment of mucositis of the genitourinary tract, particularly of the vagina, sanguinarine luteic acid salt, suitably formulated in vaginal suppositories, foams, gel and similar topical forms, proved particularly effective.

The compositions of the invention can be prepared according to conventional, well known methods, such as those described in "Remington's Pharmaceutical Handbook", Mack Publishing Co., N.Y., USA, together with suitable excipients.

The examples reported hereinbelow illustrate the invention in greater detail.

EXAMPLE I

Preparation of Sanguinarine Luteic Acid Salt 3.68 g of sanguinarine chloride is dissolved in 100 ml of ethanol and added under stirring with 3.6 g of potassium luteate and the mixture is reacted for 3 hours. The formed potassium chloride is filtered off and the solution is concentrated to small volume. 5.6 g of a salt having the following characteristics is obtained.

EXAMPLE II

1 Gram Chewable Tablets

| | | |
|---|---|---|
| 1. *Macleaya cordata* alkaloids (70%) | 2.5 mg |
| 2. Soy lecithin | 30.0 mg |
| 3. Anhydrous citric acid | 10.0 mg |
| 4. Lactose | 240.0 mg |
| 5. Mannitol | 550.0 mg |
| 6. Methylcellulose | 40.0 mg |
| 7. Palmitostearate | 50.0 mg |
| 8. Berry flavours | 40.0 mg |
| 9. Potassium acesulfame | 0.5 mg |
| 10. Talc | 10.0 mg |

EXAMPLE III

1 Gram Chewable Tablets

| | |
|---|---|
| 1. Sanguinarine bisulfate | 2.5 mg |
| 2. Soy lecithin | 30.0 mg |
| 3. Anhydrous citric acid | 10.0 mg |
| 4. Lactose | 240.0 mg |
| 5. Mannitol | 550.0 mg |
| 6. Methylcellulose | 40.0 mg |
| 7. Palmitostearate | 50.0 mg |
| 8. Berry flavours | 40.0 mg |
| 9. Potassium acesulfame | 0.5 mg |
| 10. Talc | 10.0 mg |

EXAMPLE IV

1 Gram Chewable Tablets

| | |
|---|---|
| 1. Sanguinarine bisulfate | 2.5 mg |
| 2. Soy lecithin | 30.0 mg |
| 3. Anhydrous citric acid | 10.0 mg |
| 4. Lactose | 240.0 mg |
| 5. Mannitol | 550.0 mg |
| 6. Methylcellulose | 40.0 mg |
| 7. Palmitostearate | 50.0 mg |
| 8. Berry flavours | 40.0 mg |
| 9. Potassium acesulfame | 0.5 mg |
| 10. Talc | 10.0 mg |

EXAMPLE V

1 Gram Chewable Tablets

| | |
|---|---|
| 1. Sanguinarine luteicate | 2.5 mg |
| 2. Soy lecithin | 30.0 mg |
| 3. Anhydrous citric acid | 10.0 mg |
| 4. Lactose | 240.0 mg |
| 5. Mannitol | 550.0 mg |
| 6. Methylcellulose | 40.0 mg |
| 7. Palmitostearate | 50.0 mg |
| 8. Berry flavours | 40.0 mg |
| 9. Potassium acesulfame | 0.5 mg |
| 10. Talc | 10.0 mg |

EXAMPLE VI

Soft-Gelatin Capsules for the Treatment of Vaginal Mucositis

| | |
|---|---|
| Sanguinarine luteicate | 10 mg |
| soy lecithin | 50 mg |
| beeswax | 50 mg |
| vegetable oil q.s. to | 800 mg |

EXAMPLE VII

Cream (Oil in Water Emulsion) for Inside and Outside Vaginal Mucositis

| | |
|---|---|
| 1. Sanguinarine bisulfate | 200.0 mg |
| 2. *Echinacea angustifolia* lipophilic extract | 100.0 mg |
| 3. Propylene glycol | 10.00 g |
| 4. Soy lecithin | 50 mg |
| 5. Beeswax | 50 mg |
| 6. Isopropyl myristate | 5.00 g |
| 7. Cetyl alcohol | 5.00 g |
| 8. Polysorbate 80 | 3.00 g |
| 9. Carbomer | 0.40 g |
| 10. Methyl para hydroxy benzoate | 0.10 g |
| 11. Propyl para hydroxy benzoate | 0.05 g |
| 12. Purified water q.s. To | 100 g |

EXAMPLE VIII

Vaginal Suppository

| | |
|---|---|
| 1. Sanguinarine bisulfate | 3 mg |
| 2. Fatty acids glycerides q.s. to | 2.0 g |

The invention claimed is:

1. Formulations consisting of sanguinarine or chelerythrine as luteic acid salts in admixture with suitable carriers and/or excipients for the treatment and/or prevention of mucositis.

2. Formulations consisting of
   sanguinarine or chelerythrine as luteic acid salts; and
   natural or synthetic isobutylamides.

3. Formulations as claimed in claim 2, wherein isobutylamides are contained in *Echinacea angustifolia* lipophilic extract.

4. Formulations consisting of sanguinarine or chelerythrine as luteic acid salts in admixture with suitable carriers and/or excipients for the treatment and/or prevention of mucositis said formulation being in the form of tablets, granulates, capsules or chewable tablets, chewing gum, creams, ointments, foams, vaginal suppositories, patches.

5. Chelerythrine luteic acid salts.

6. Sanguinarine luteic acid salts.

7. A method for treatment of mucositis comprising administering an effective amount of sanguinarine or chelerythrine as luteic acid salts to a patient in need thereof.

8. Method of claim 7, wherein said effective amount ranges from 1 to 20 mg.

9. Method of claim 7, wherein mucositis is induced by chemotherapy, radiotherapy or immunosuppressive treatment.

10. Method of claim 7, wherein mucositis is buccal or vaginal mucositis.

11. Method of claim 9, further comprising administering natural or synthetic isobutylamides.

\* \* \* \* \*